United States Patent

Takahashi et al.

(10) Patent No.: US 6,777,570 B2
(45) Date of Patent: Aug. 17, 2004

(54) PROCESS FOR PRODUCING NORBORNENE DERIVATIVE HAVING ORGANOSILYL GROUP

(75) Inventors: Hiroko Takahashi, Kanagawa (JP); Takako Takahashi, Kanagawa (JP); Taketoshi Naito, Kanagawa (JP); Shuji Ichikawa, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/670,515

(22) Filed: Sep. 26, 2003

(65) Prior Publication Data

US 2004/0063982 A1 Apr. 1, 2004

(30) Foreign Application Priority Data

Sep. 30, 2002 (JP) ........................................ 2002-286353
May 28, 2003 (JP) ........................................ 2003-150810

(51) Int. Cl.[7] .................................................. C07F 7/08
(52) U.S. Cl. ........................................................ 556/480
(58) Field of Search ........................................ 556/480

(56) References Cited

PUBLICATIONS

Robert F. Cunico, "The Diels–Alder Reaction of α, β–Unsaturated Trihalosilanes with Cyclopentadiene", J. Organ. Chem., vol. 36, No. 7, 1971, pp. 929–932.

Henry G. Kuivila, et al., "Trimethylsilyl–Substituted Norbornenes, Norbornanes, and Nortricyclene[1]" J. Org. Chem., vol. 29, Oct. 1964, pp. 2845–2851.

Kohei Tamao, et al., "Organofluorosilicates in Organic Synthesis", Journal of Organometallic Chemistry, vol. 225, 1982, pp. 151–162.

Primary Examiner—Samuel Barts
(74) Attorney, Agent, or Firm—Oblon, Spivak, McClelland, Maier & Neustadt, P.C.

(57) ABSTRACT

A process for producing a norbornene derivative having an organosilyl group suitable as a synthetic intermediate for pesticides and medicaments and for production of polyolefin polymers, particularly polyolefin polymers having a good adhesiveness with metals or insulating inorganic materials in high yields with a satisfactory purity. A process for producing a norbornene derivative having an organosilyl group represented by the general formula (3):

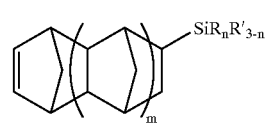

(3)

wherein R each represents an alkyl group or an aryl group, R' represents an alkyl group or an aryl group, n represents an integer of 0 to 2 and m represents an integer of 0 or more, which comprises reacting a compound represented by the general formula (1):

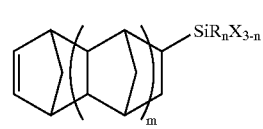

(1)

wherein R, n and m have the same meanings as above, and X represents a halogen atom,
with a Grignard agent represented by the general formula (2):

R'MgCl (2)

wherein R' has the same meaning as above.

2 Claims, No Drawings

PROCESS FOR PRODUCING NORBORNENE DERIVATIVE HAVING ORGANOSILYL GROUP

FIELD OF THE INVENTION

The present invention relates to a process for producing a norbornene derivative having an organosilyl group suitable as a synthetic intermediate for pesticides and medicaments and as a monomer for use in polyolefin polymers, particularly polyolefin polymers having a good adhesiveness with metals or insulating inorganic materials.

BACKGROUND OF THE INVENTION

As processes for producing a norbornene derivative having an organosilyl group, there is known a process wherein a trialkylvinylsilane and cyclopentadiene are subjected to a Diels-Alder reaction (cf. Non-patent literature 1) and a process wherein norbornadiene and a trialkylsilane are subjected to a hydrosilylation reaction (cf. Non-patent literature 2). However, these processes are not satisfactory as industrial processes because yields are as low as about 50% in both cases and also the processes require special equipments for the production since the reactions are carried out in a closed vessel having pressure resistance under a high temperature of 170° C. or higher.

In addition, the process of Non-patent literature 2 is not preferred because an expensive platinum catalyst should be used.

Furthermore, a process for producing the derivative by a Grignard reaction between trichlorosilylnorbornene and methylmagnesium bromide (Non-patent literature 3) affords a by-product having a boiling point close to that of the product, and hence is unsatisfactory as an industrial process for producing highly pure trimethylsilylnorbornene.

Moreover, the process using a substrate having a halogen atom such as chlorine atom in the molecule as the above compound is not preferred, for example, in the field where an insulating inorganic material or the like is employed, when a large amount of the halogen atom remains in the product. Accordingly, a process for producing the norbornene derivative having a higher purity has been desired.

Non-patent literature 1:
J. Org. Chem., Vol. 36 (1971), p. 929
Non-patent literature 2:
J. Org. Chem., Vol. 29 (1964), p. 2845
Non-patent literature 3:
J. Organomet. Chem., Vol. 225 (1982), p. 151

SUMMARY OF THE INVENTION

As mentioned above, in the production of a norbornene derivative having an organosilyl group, it is desired to develop a process for producing the product having a high purity in an industrially convenient and effective manner.

As a result of intensive studies for overcoming the above problems, the present inventors have found that the use of a chlorine atom as a halogen atom of a Grignard reagent results in excellent selectivity and yield of the reaction, and thus have accomplished the invention.

Namely, the gist of the invention lies in a process for producing a norbornene derivative having an organosilyl group represented by the following general formula (3):

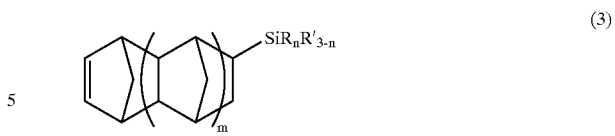

wherein R each represents an alkyl group or an aryl group, R' represents an alkyl group or an aryl group, n represents an integer of 0 to 2 and m represents an integer of 0 or more, which comprises reacting a compound represented by the following general formula (1):

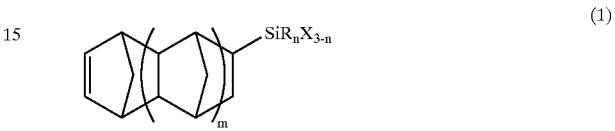

wherein R, n and m have the same meanings as above, and X represents a halogen atom,
with a Grignard agent represented by the following general formula (2):

$$R'MgCl \qquad (2)$$

wherein R' has the same meaning as above.

DETAILED DESCRIPTION OF THE INVENTION

In the invention, an objective norbornene derivative having an organosilyl group is produced by reacting a norbornene compound having a halosilyl group with a specific Grignard agent.

Starting Material for Reaction

The norbornene compound having a halosilyl group to be used as a starting material for the invention is represented by the above general formula (1).

In the formula, R is specifically a linear, branched or cyclic alkyl group such as a methyl, ethyl, n-propyl, isopropyl, n-butyl, s-butyl, n-pentyl, n-hexyl, n-heptyl or n-octyl group; or an aryl group such as a phenyl, tolyl or xylyl group. Of these, the alkyl group has preferably from 1 to 8 carbon atoms, more preferably from 1 to 4 carbon atoms. Moreover, the aryl group has preferably from 6 to 8 carbon atoms.

X is a halogen atom such as a chlorine, bromine, or iodine atom, and is preferably a chlorine atom.

n is an integer of 0 to 2, and is preferably 0 or 1, particularly preferably 0.

m is an integer of 0 or more, and is preferably 0 or 1, particularly preferably 0.

The above compound can be easily produced by a Diels-Alder reaction between a vinylhalosilane ($CH_2$=CH—$SiR_nX_{3-n}$) and cyclopentadiene or dicyclopentadiene. In the Diels-Alder reaction between cyclopentadiene and a vinylhalosilane, the reaction rate remarkably is increased by introducing the electron-withdrawing halogen atom and as a result, it becomes possible to lower the reaction temperature.

Examples of preferred vinylhalosilane ($CH_2$=CH—$SiR_nX_{3-n}$) include vinyltrichlorosilane, dichloromethylvinylsilane, vinylphenyldichlorosilane, chlorodimethylsilane, diphenylvinylchlorosilane, vinylethyldichlorosilane, vinylphenylmethylchlorosilane, vinyldimethylfluorosilane, and vinyloctyldichlorosilane.

As reaction operations, a procedure generally performed in a Diels-Alder reaction may be employed. For example, in the case of using cyclopentadiene, the reaction is completed under an atmosphere of an inert gas, such as nitrogen gas or argon gas at a temperature of 30 to 150° C., preferably 50 to 100° C. for about 0.5 to 24 hours. Alternatively, in the case of using dicyclopentadiene, it is necessary to carry out the reaction at a higher temperature, for example, from 180 to 220° C.

The reaction may be carried out without solvent but is preferably carried out with a solvent in view of selectivity of the reaction. The solvent to be used is preferably a hydrocarbon solvent such as toluene or an ether solvent such as tetrahydrofuran.

In the case that m is 1 or more, the corresponding compound can be obtained by repeating the Diels-Alder reaction with cyclopentadiene two times or more times.

Grignard Agent

The Grignard reagent to be used in the invention is represented by the above general formula (2) and it is one characteristic feature of the invention that a chlorine atom is used as a halogen atom for the Grignard reagent.

In the formula, R' may include the same groups as those exemplified as R in the above general formula (1). Of these, preferred is an alkyl group.

Preferred specific examples of the above Grignard reagent include reagents containing a linear, branched or cyclic alkyl group having 1 to 6 carbon atoms, such as methylmagnesium chloride, ethylmagnesium chloride, n-propylmagnesium chloride, i-propylmagnesium chloride, n-butylmagnesium chloride, i-butylmagnesium chloride, sec-butylmagnesium chloride, t-butylmagnesium chloride, n-pentylmagnesium chloride, neopentylmagnesium chloride, 1,1-dimethylpropylmagnesium chloride, n-hexylmagnesium chloride, 2-hexylmagnesium chloride, 3-hexylmagnesium chloride, 2-ethylbutylmagnesium chloride, n-heptylmagnesium chloride, 2-heptylmagnesium chloride, 3-heptylmagnesium chloride, 4-heptylmagnesium chloride, cyclohexylmethylmagnesium chloride, n-octylmagnesium chloride, 2-ethylhexylmagnesium chloride, cyclopropylmagnesium chloride, cyclopentylmagnesium chloride and cyclohexylmagnesium chloride. Of these, preferred is a reagent containing a linear, branched or cyclic alkyl group having 1 to 4 carbon atoms, and particularly preferred is a reagent containing a linear alkyl group having 1 to 4 carbon atoms.

The Grignard reagent may be used as a commercially available one or may be prepared in accordance with a known method from a corresponding alkyl chloride. Namely, it is obtained by placing activated magnesium metal in an ether solvent such as anhydrous diethyl ether or anhydrous tetrahydrofuran at a temperature of 0 to 100° C., preferably 10 to 50° C., adding dropwise the alkyl chloride under stirring, and continuing the stirring for further 0.1 to 8 hours.

The magnesium metal to be used in the reaction may be commercially available tape-shaped or chip-shaped one and the amount thereof to be used is from 1 to 2 molar equivalents to the alkyl chloride. Moreover, prior to the reaction, it is effective for smooth proceeding of the subsequent reaction to mix magnesium metal in a nitrogen atmosphere or under reduced pressure for the purpose of activating the metal or to add a minute amount of iodine or dibromoethane. With regard to the solvent to be used, a similar result can be obtained in tetrahydrofuran or diethyl ether alone or in a mixture thereof with benzene or toluene.

Method for Reaction

Any method generally used for the general Grignard reaction may be suitably used for the reaction between the norbornene compound having a halosilyl group represented by the above general formula (1) with the Grignard reagent represented by the above general formula (2).

The amount of the Grignard reagent for use in the reaction is usually 0.8 molar equivalent or more, preferably 0.95 molar equivalent or more. The upper limit is 2.0 molar equivalents or less, preferably 1.2 molar equivalents or less. This range of the ratio is preferable in view of economical efficiency and reactivity.

The solvent to be used is not restricted as far as it dissolves the starting norbornene compound and does not inhibit the reaction. Preferable solvent is an organic ether solvent such as diethyl ether, tetrahydrofuran, diisopropyl ether or tert-butyl methyl ether; or a mixed solvent of the ether solvent with the other organic solvent, e.g., an aromatic hydrocarbon such as benzene, toluene or xylene.

The above ether solvent may be used singly or as a mixture of two or more of them. Particularly preferred is diethyl ether or tetrahydrofuran.

The above-mentioned other organic solvent may be used in an amount within the range where the object of the invention is not inhibited. The volume ratio of the ether solvent to the hydrocarbon solvent is preferably from 10:1 to 1:10.

The amount of the organic solvent to be used is preferably 100 parts by weight or more, more preferably from 200 to 2500 parts by weight based on 100 parts by weight of the starting norbornene compound.

The mode of the reaction is not particularly restricted, and the objective norbornene derivative can be obtained in high yields by either of a method wherein the Grignard reagent is dissolved in the solvent and then the norbornene compound having a halosilyl group is added thereto or a method wherein the norbornene compound having a halosilyl group is dissolved in the solvent and then the Grignard reagent is added thereto.

The reaction temperature may vary depending on the starting material and the amount of the Grignard reagent used, but may be within a temperature range where a Grignard reaction is generally conducted. Specifically, the reaction is usually conducted in the range of −20° C. to a reflux temperature of the solvent, but is conducted preferably at 0° C. or higher, more preferably at 30° C. or higher since problems in reaction rate and facility cost may arise when the temperature is too low.

After completion of dropwise addition of the Grignard reagent, the reaction may be usually completed within about 1 to 15 hours. Thus, after the reaction is conducted for a predetermined period of time, the reaction liquid is poured into a dilute aqueous acidic solution such as saturated ammonium chloride solution or dilute hydrochloric acid to inactivate the unreacted reagent and then subjected to usual operations for isolation, e.g., extraction with an organic solvent and concentration.

Moreover, the norbornene derivative having an organosilyl group may be also purified by means of distillation, chromatography, or the like, if necessary.

The thus-obtained norbornene derivative having an organosilyl group represented by the above general formula (3) is a compound represented by the above general formula (1) wherein X is replaced by R'. Preferred specific examples thereof include trimethyl-5-norbornen-2-yl-silane, triethyl-5-norbornen-2-yl-silane, diethylmethyl(5-norbornen-2-yl)-silane, dipheylmethyl(5-norbornen-2-yl)-silane, phenyldimethyl(5-norbornen-2-yl)-silane, ethyldimethyl(5-norbornen-2-yl)-silane, dimethyloctyl(5-norbornen-2-yl)-silane, diphenylethyl(5-norbornen-2-yl)-silane, phenyldiethyl(5-norbornen-2-yl)-silane, diethyloctyl(5-norbornen-2-yl)-silane, phenylethylmethyl(5-norbornen-2-yl)-silane, tripropyl-5-norbornen-2-yl-silane, dipropylmethyl(5-norbornen-2-yl)-silane, diphenylpropyl(5-norbornen-2-yl)-silane, propyldimethyl(5-norbornen-2-yl)-silane, phenyldipropyl(5-norbornen-2-yl)-silane, ethyldipropyl(5-norbornen-2-yl)-silane, phenylmethylpropyl(5-norbornen-2-yl)-silane, dimethylpropyl(5-norbornen-2-yl)-silane, and dipropyloctyl(5-norbornen-2-yl)-silane.

The norbornene derivative having an organosilyl group obtainable by the process of the invention has a high purity, e.g., 96% or more, preferably 97% or more, more preferably 98% or more, further preferably 99% or more.

In particular, the unreacted starting material and a by-product containing a halogen atom as reaction intermediates are undesirable compounds in the field of insulating inorganic materials and the like which is one of applications of the norbornene derivative having an organosilyl group obtained by the invention but these compounds are hardly produced.

In addition, a hydroxysilyl compound formed through hydrolysis of the above compound having a remaining halogen atom in the molecule during the post-treatment process, the halogen atom being thereby converted into a hydroxyl group, generally has similar physical properties to those of the objective compound. Therefore, it is difficult to separate the compounds from each other by operations for separation and purification frequently used industrially, such as distillation and crystallization. However, according to the process of the invention, it is possible to control the contaminating amount of the hydroxysilyl compound and disiloxane compound obtained by dimerization of the hydroxysilyl compound to 4% or less, preferably 3% or less, more preferably 2% or less, particularly preferably 1% or less.

The following will describe the invention in more detail with reference to Examples but the invention is not limited thereto.

Production Example 1
Synthesis of Trichlorosilylnorbornene (X=Cl, n=0, m=0)

Vinyltrichlorosilane (0.845 mol) was reacted with cyclopentadiene (67 g: 1.01 mol) at 70° C. for 3 hours under a nitrogen atmosphere. Unreacted vinyltrichlorosilane and cyclopentadiene were removed by fractional distillation, and then trichlorosilylnorbornene (boiling point: 108–110° C./35 mmHg) was obtained in a yield of 75% by separating trichlorosilylnorbornene.

EXAMPLE 1

Under a nitrogen stream, in a 1 L four-neck flask were placed 141.3 ml (294 mmol: 3.80 equivalents) of a tetrahydrofuran solution of 2.08N methylmagnesium chloride and 200 ml of tetrahydrofuran, and the whole was heated under gentle reflux. Thereto was added dropwise a tetrahydrofuran solution (10 ml) of 17.6 g (77.3 mmol) of trichlorosilylnorbornene. After completion of the dropwise addition, the resulting mixture was heated under reflux for further 1 hour. After cooling, 50 ml of saturated ammonium chloride solution and 80 ml of water were added thereto. After separation of the organic layer, tetrahydrofuran was removed by evaporation, followed by extraction with 50 ml of ethyl acetate. The organic layer was washed twice with 50 ml of saturated brine and dried over anhydrous magnesium sulfate. Then, the solvent was removed by evaporation to obtain 11.8 g of trimethylsilylnorbornene (yield 92%). When the product was analyzed by gas chromatography and mass spectrometry, the trimethylsilylnorbornene (M$^+$=166) was found to have a purity of 99.5% (gas chromatographic analysis: retention time 8.3 minutes). Moreover, it was confirmed that, as a by-product, hydroxydimethylsilylnorbornene was formed in an amount of 0.5% (gas chromatographic analysis: retention time 9.2 minutes).

The analytical conditions in the above chromatography were as follows.

Apparatus: GC-14A manufactured by Shimadzu Corporation

Column: NB-5 (0.32 mm I.D.×30 M, df=0.4 μm) (manufactured by GL Science)

Column temperature: maintained at 50° C. for 5 minutes, then elevated at a rate of 20° C./minute, and then maintained at 250° C. for further 10 minutes Injection temperature and Detector temperature: 280° C.

COMPARATIVE EXAMPLE 1

Reaction and post-treatment were conducted in the same manner as in Example 1 with the exception that methylmagnesium bromide was used instead of methylmagnesium chloride, and thereby 11.4 g of trimethylsilylnorbornene was obtained (yield 89%). When the product was analyzed in the same manner as in Example 1, the trimethylsilylnorbornene was found to have a purity of 95.4%. Moreover, it was confirmed that, as by-products, hydroxydimethylsilylnorbornene and high-boiling products such as disiloxane were formed in an amount of 3.0% and 1.6%, respectively.

COMPARATIVE EXAMPLE 2

Reaction and post-treatment were conducted in the same manner as in Example 1 with the exception that methylmagnesium iodide was used instead of methylmagnesium chloride, and thereby 10.0 g of trimethylsilylnorbornene was obtained (yield 78%). When the product was analyzed in the same manner as in Example 1, the trimethylsilylnorbornene was found to have a purity of 89.5%. Moreover, it was confirmed that as by-products, high-boiling products such as disiloxane and a product (M$^+$=152) (gas chromatographic analysis: retention time 9.0 minutes) which is difficult to separate and whose structure was unidentified were formed in an amount of 9.5% and 1.0%, respectively.

EXAMPLE 2

Under a nitrogen stream, in a 50 mL four-neck flask were placed 9.6 ml (20 mmol: 4 equivalents) of a tetrahydrofuran solution of 2.08N methylmagnesium chloride and 10 ml of tetrahydrofuran, and the whole was heated under gentle reflux. Thereto was added dropwise a tetrahydrofuran solution (1 ml) of 1.13 g (5 mmol) of trichlorosilylnorbornene. After completion of the dropwise addition, the resulting mixture was heated under reflux for further 1 hour. After cooling, 3 ml of saturated ammonium chloride solution and 5 ml of water were added thereto. After separation of the organic layer, tetrahydrofuran was removed by evaporation, followed by extraction with 10 ml of ethyl acetate. The organic layer was washed twice with 10 ml of saturated brine and dried over anhydrous magnesium sulfate. Then, the solvent was removed by evaporation to obtain 0.68 g of trimethylsilylnorbornene (yield 82%). When the product was analyzed in the same manner as in Example 1, the trimethylsilylnorbornene was found to have a purity of 99.6%. Moreover, it was confirmed that, as a by-product, hydroxydimethylsilylnorbornene was formed in an amount of 0.4%.

EXAMPLE 3

Under a nitrogen stream, in a 500 mL four-neck flask was placed 113.9 ml (237 mmol: 3.85 equivalents) of a tetrahydrofuran solution of 2.08N methylmagnesium chloride, and the whole was heated under gentle reflux. Thereto was added dropwise a tetrahydrofuran solution (14 ml) of 14 g (61.5 mmol) of trichlorosilylnorbornene. After completion of the dropwise addition, the resulting mixture was heated under reflux for further 1 hour. After cooling, 26 ml of saturated ammonium chloride solution and 62 ml of water were added thereto. After separation of the organic layer, tetrahydrofuran was removed by evaporation, followed by extraction with 50 ml of ethyl acetate. The organic layer was washed twice with 50 ml of saturated brine and dried over anhydrous magnesium sulfate. Then, the solvent was removed by evaporation to obtain 9.5 g of trimethylsilylnorbornene (yield 92%). When the product was analyzed in the same manner as in Example 1, the trimethylsilylnorbornene was found to have a purity of 99.8%. Moreover, it was confirmed that, as a by-product, hydroxydimethylsilylnorbornene was formed in an amount of 0.2%.

According to the process of the invention, a norbornene derivative having an organosilyl group suitable as a synthetic intermediate for pesticides and medicaments and for production of polyolefin polymers, particularly polyolefin polymers having a good adhesiveness with metals or insulating inorganic materials can be produced in high yields with a satisfactory purity.

While the invention has been described in detail and with reference to specific embodiments thereof, it will be apparent to one skilled in the art that various changes and modifications can be made therein without departing from the scope thereof.

This application is based on Japanese patent applications No. 2002-286353 filed Sep. 30, 2002 and No. 2003-150810 filed May 28, 2003, the entire contents thereof being hereby incorporated by reference.

What is claimed is:

1. A process for producing a norbornene derivative having an organosilyl group represented by the following general formula (3):

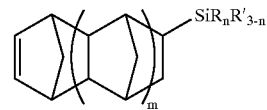

(3)

wherein R each represents an alkyl group or an aryl group, R' represents an alkyl group or an aryl group, n represents an integer of 0 to 2 and m represents an integer of 0 or more, which comprises reacting a compound represented by the following general formula (1):

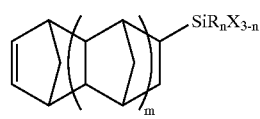

(1)

wherein R, n and m have the same meanings as above, and X represents a halogen atom, with a Grignard agent represented by the following general formula (2):

(2)

wherein R' has the same meaning as above.

2. The process according to claim 1, wherein n is 0.

* * * * *